(12) United States Patent
Schlaudraff (10) Patent No.: US 9,857,331 B2
(45) Date of Patent: Jan. 2, 2018

(54) LASER MICRODISSECTION SYSTEM AND EXAMINATION METHOD FOR SAMPLES CONTAINING NUCLEIC ACID

(71) Applicant: LEICA MICROSYSTEMS CMS GMBH, Wetzlar (DE)

(72) Inventor: Falk Schlaudraff, Butzbach, DE (US)

(73) Assignee: LEICA MICROSYSTEMS CMS GMBH, Wetzlar (DE)

( * ) Notice: Subject to any disclaimer, the term of this patent is extended or adjusted under 35 U.S.C. 154(b) by 30 days.

(21) Appl. No.: 14/901,727

(22) PCT Filed: Jul. 1, 2014

(86) PCT No.: PCT/EP2014/063920
§ 371 (c)(1),
(2) Date: Dec. 29, 2015

(87) PCT Pub. No.: WO2015/000879
PCT Pub. Date: Jan. 8, 2015

(65) Prior Publication Data
US 2016/0370315 A1    Dec. 22, 2016

(30) Foreign Application Priority Data

Jul. 1, 2013  (DE) .................. 10 2013 212 811

(51) Int. Cl.
*G01N 27/453*   (2006.01)
*G01N 27/447*   (2006.01)
(Continued)

(52) U.S. Cl.
CPC ... *G01N 27/44721* (2013.01); *C12N 15/1003* (2013.01); *G01N 1/286* (2013.01);
(Continued)

(58) Field of Classification Search
CPC ............ G02B 21/0004; G02B 21/0012; G02B 21/0016; G02B 21/0028; G02B 21/0036;
(Continued)

(56) References Cited

U.S. PATENT DOCUMENTS 5,671,086 A    9/1997 Parvin et al.
6,907,798 B2 *  6/2005 Ganser ................. G01N 1/04
                                                73/864.41

(Continued)

FOREIGN PATENT DOCUMENTS

DE          10057292 A1    7/2002
DE          10322348 B4    5/2005
(Continued)

OTHER PUBLICATIONS

Product data for the Trevigen® 96-well CometSlide™, 2012, downloaded May 12, 2017 from https://trevigen.com/docs/protocol/protocol_4253-096-03.pdf.*

(Continued)

*Primary Examiner* — Alexander S Noguerola
(74) *Attorney, Agent, or Firm* — Leydig, Voit & Mayer, Ltd.

(57) ABSTRACT

A laser microdissection includes a microscope having an incident-light device, a microscope objective, and a laser unit operable to produce a laser beam having a beam path extending through the incident-light device and through the microscope objective and intersecting an object plane of the microscope objective at an adjustable intersection point. The laser microdissection systems further includes an electrophoresis unit located below the object plane and containing an electrophoresis gel including one or more gel pockets, and a positioning device operable to position the electrophoresis gel in parallel with the object plane of the microscope objective and relative to a defined reference position (Continued)

such that dissectates of a sample that can be arranged in the object plane can be collected in the one or more gel pockets. The electrophoresis unit is operable to be attached by a coupling device. The dissectates are obtained via the laser beam.

14 Claims, 3 Drawing Sheets

(51) Int. Cl.
　　*G02B 21/00* (2006.01)
　　*G02B 21/26* (2006.01)
　　*C12N 15/10* (2006.01)
　　*G01N 1/28* (2006.01)
　　*G02B 21/32* (2006.01)
　　*G02B 21/18* (2006.01)

(52) U.S. Cl.
　　CPC ..... *G01N 1/2813* (2013.01); *G01N 27/44743* (2013.01); *G01N 27/44782* (2013.01); *G02B 21/0016* (2013.01); *G02B 21/0028* (2013.01); *G02B 21/0048* (2013.01); *G02B 21/18* (2013.01); *G02B 21/26* (2013.01); *G02B 21/32* (2013.01); *G01N 2001/284* (2013.01); *G01N 2001/2886* (2013.01)

(58) Field of Classification Search
　　CPC ........ G02B 21/24; G02B 21/26; G02B 21/32; G01N 27/44704; G01N 27/44721; G01N 27/44743; G01N 27/44752; G01N 27/44782; G01N 27/453; C12N 15/1003
　　See application file for complete search history.

(56) References Cited

U.S. PATENT DOCUMENTS

| | | |
|---|---|---|
| 2002/0061261 A1 | 5/2002 | Pfeifer et al. |
| 2003/0133190 A1 | 7/2003 | Weiss |
| 2004/0247777 A1 | 12/2004 | Ringeisen et al. |
| 2008/0032034 A1 | 2/2008 | Niyaz et al. |
| 2008/0069737 A1 | 3/2008 | Fasulka |
| 2008/0199929 A1 | 8/2008 | Yeung |
| 2009/0272657 A1 | 11/2009 | Bhatia et al. |
| 2012/0058467 A1 | 3/2012 | Thomas et al. |
| 2013/0105320 A1* | 5/2013 | Samson ........... G01N 27/44756 204/461 |
| 2013/0234015 A1 | 9/2013 | Becker et al. |

FOREIGN PATENT DOCUMENTS

| | | |
|---|---|---|
| DE | 102004041941 B4 | 3/2006 |
| DE | 10358565 B4 | 6/2007 |
| DE | 112006001276 T5 | 4/2008 |
| DE | 102009016512 A1 | 10/2010 |
| EP | 1276586 B1 | 1/2003 |
| WO | WO 9814816 A1 | 4/1998 |
| WO | WO 02010751 A2 | 2/2002 |
| WO | WO 2008052655 A1 | 5/2008 |

OTHER PUBLICATIONS

Wood, D.K. et al.: "single cell trapping and DNA damage analysis using microwell arrays", Proc. Natl. Acad. Sci USA, vol. 107, No. 22, Jun. 1, 2010, pp. 10.008-10.013.

* cited by examiner

LASER MICRODISSECTION SYSTEM AND EXAMINATION METHOD FOR SAMPLES CONTAINING NUCLEIC ACID

CROSS REFERENCE TO RELATED APPLICATIONS

This application is a U.S. National Stage Application under 35 U.S.C. §371 of International Application No. PCT/EP2014/063920 filed on Jul. 1, 2014, and claims benefit to German Patent Application No. DE 10 2013 212 811.8 filed on Jul. 1, 2013. The International Application was published in German on Jan. 8, 2015 as WO 2015/000879 A1 under PCT Article 21(2).

FIELD

The present invention relates to a laser microdissection system, to an electrophoresis unit for a laser microdissection system, and to a corresponding examination method for nucleic-acid-containing samples.

BACKGROUND

Methods for processing biological samples by means of laser microdissection have been in existence since the mid-1970s (see e.g. Isenberg, G. et al.: Cell surgery by laser micro-dissection: a preparative method. Journal of Microscopy, Vol. 107, 1976, pages 19-24) and have been continuously developed ever since.

In laser microdissection, cells, tissue regions and the like can be isolated from a sample ("object", "preparation") and obtained as dissectates. A particular advantage of laser microdissection is that the sample comes into brief contact with the laser beam, and this barely alters the sample. In this context, the dissectates can actually be obtained in various ways (see e.g. Bancroft, J. D. and Gamble, M.: Theory and Practice of Histological Techniques. Elsevier Science, 2008, page 575, Chapter "Laser Microdissection").

In known methods, for example, a dissectate can be isolated from a sample by means of an infrared or ultraviolet laser beam, which dissectate falls into a suitable dissectate collection container as a result of gravity. In the process, the dissectate can also be cut out from the sample together with an adherent membrane. By contrast, in laser capture microdissection, a thermoplastic membrane is heated by means of an appropriate laser beam. In the process, the membrane fuses with the desired region of the sample and can be removed in a subsequent step by being torn off. A further alternative is to fix the dissectate to a lid of a dissectate collection container by means of the laser beam. In known inverted microscope systems for laser microdissection, dissectates catapulted upwards can also be fixed to the base of a dissectate collection container provided with an adhesive coating.

Known microscope systems for laser microdissection, as known for example from WO 98/14816 A1, comprise an incident-light device, into the beam path of which a laser beam is coupled. The laser beam is focused onto the sample, which rests on a microscope stage that can move automatically by means of a motor, by the microscope objective used in each case. A cut line is produced by the microscope stage being moved during the cutting in order to move the sample relative to the stationary laser beam. This, however, is disadvantageous inter alia in that the sample cannot be easily viewed while the cut line is being produced since said line moves in the field of vision and the image appears blurred.

Laser microdissection systems comprising laser deflection devices or laser scanning devices designed to deflect the laser beam or the incident point thereof over the stationary sample are therefore more advantageous. Laser microdissection systems of this type, which also offer particular advantages in the context of the present invention, are explained in detail below. A particularly advantageous laser microdissection system which comprises, in the laser beam path, a laser scanning device having glass wedges which can move relative to one another, is described for example in the above-mentioned patent EP 1 276 586 B1.

In both cases, that is both in laser microdissection systems in which the microscope stage is moved and in laser microdissection systems which comprise a laser scanning device, pulsed lasers are generally used, a hole being made in the sample by each laser pulse. A cut line is produced by making such holes next to each other, optionally with an appropriate overlap.

The laser microdissection can be used to obtain single cells or defined tissue regions, in other words dissectates of nucleic-acid-containing samples. Corresponding dissectates can then undergo various molecular biology analysis methods.

To check for DNA damage (in particular individual or double strand breakages, multiplications, deletions, dimerisations, etc.) in single cells or particular tissue regions, single-cell gel electrophoresis is known, for example (see e.g. Wood, D. K. et al.: Single-cell trapping and DNA damage analysis using microwell arrays, Proc. Natl. Acad. Sci. USA, Vol. 107, 2010, pages 10.008-10.013). Single-cell gel electrophoresis (also referred to as the comet assay) is based on the fact that corresponding DNA damage, for example strand breakages in the DNA, cause changes to the geometric properties thereof and thus the migration behaviour or mobility in the electrophoresis.

In this respect, the general observations are that damaged DNA fragments are more mobile in the conventionally used agarose gels than undamaged DNA fragments. This can be seen in a comet-tail-like migration image. By means of single-cell gel electrophoresis, a plurality of different DNA lesions can be detected, it also being possible, for example, to use DNA repair enzymes or other reagents to show up damage which is undetectable per se. An overview of this can be found in the above-mentioned article by Wood et al.

However, single-cell gel electrophoresis can conventionally only be carried out at low throughputs and with relatively poor reproducibility. The image processing and analysis methods used are complex, laborious and potentially susceptible to errors. The article by Wood et al. proposes a method for high-throughput single-cell gel electrophoresis, wherein an electrophoresis gel having a number of gel pockets is used and can subsequently undergo standard high-throughput screening techniques. In particular, however, it is not possible to use the method disclosed therein to specifically place particular cells or cell types into specific gel pockets. In the method, the entire gel is covered with a cell suspension and the respective cells settle at random in the gel pockets provided in each case.

SUMMARY

In an embodiment, the present invention provides a laser microdissection system. The laser microdissection system includes a microscope having an incident-light device, a microscope objective, and a laser unit operable to produce a laser beam having a beam path extending through the incident-light device and through the microscope objective and intersecting an object plane of the microscope objective at an adjustable intersection point. The laser microdissection systems further includes an electrophoresis unit disposed below the object plane and containing an electrophoresis gel including one or more gel pockets, and a positioning device operable to position the electrophoresis gel in parallel with the object plane and relative to a defined reference position such that dissectates of a sample that can be disposed in the object plane can be collected in the one or more gel pockets. The electrophoresis unit is operable to be attached by a coupling device. The dissectates are obtained using the laser beam of the laser unit.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

In various embodiments, the present invention provides a laser microdissection system, an electrophoresis unit for such a laser microdissection system, and a corresponding examination method for nucleic-acid-containing samples.

In an embodiment, the invention seeks to improve the execution of corresponding single-cell gel electrophoresis methods. In an embodiment, the present invention can be used in methods in which a dissectate is separated from a sample and collected in a dissectate collection container arranged therebelow. In an embodiment, the invention is suitable for non-contact collection systems for dissectates.

In an embodiment, the invention improves laser microdissection systems that are known per se. Such laser microdissection systems include a microscope which has an incident-light device, a microscope objective and a laser unit, a beam path of a laser beam of the laser unit extending through the incident-light device and through the microscope objective and intersecting an object plane of the microscope objective at an adjustable intersection point. In an embodiment, a laser microdissection system is distinguished in that, below the object plane, an electrophoresis unit containing an electrophoresis gel is attached or can be attached by means of coupling means, the electrophoresis gel having at least one gel pocket and the laser microdissection system comprising positioning means for positioning the electrophoresis gel in parallel with the object plane and relative to a defined reference position so that dissectates, obtained by means of the laser beam of the laser unit, of a sample which can be arranged in the object plane can be collected in the at least one gel pocket.

In an embodiment, a laser microdissection system includes a microscope having an incident-light device for focusing a laser beam through a microscope objective of the microscope onto a sample to be dissected, in particular a nucleic-acid-containing sample, and means for separating a dissectate from the nucleic-acid-containing sample by means of the focused laser beam.

In this case, an embodiment of the invention can be used in particular in non-contact laser microdissection systems. These are distinguished in that a dissectate is not fixed to membranes and the like, but rather falls downwards out of the sample as a result of gravity. In the process, the sample is arranged in upright systems on the underside of an object support and is processed therethrough using the laser beam from the top side thereof.

By means of the incident-light device, a laser beam from a laser source is coupled into the observation beam path of the microscope. The laser beam is focused onto the sample by the microscope objective that is also used to view the nucleic-acid-containing sample.

To prevent any miscomprehension, it is emphasised at this juncture that a laser microdissection system used in the context of an embodiment of the invention is used with nucleic-acid-containing samples which have already been prepared for use in microscopy. In this respect, these may for example be microsections which are separated from a larger block of tissue by means of a microtome. A block of tissue of this type may for example be an adherent organ or a biopsy of a corresponding organ. The laser microdissection system according to an embodiment of the invention is therefore not used to obtain nucleic-acid-containing samples, but to process them and to isolate certain regions thereof. It goes without saying that an embodiment of the invention can also be used with other nucleic-acid-containing samples that are not obtained by means of a microtome, for example using smears, macerations, etc.

Microtomes are exclusively used to prepare microscopic samples. To do so, microtomes can also comprise lasers. As mentioned above, the sections obtained by means of a microtome are placed on an object support and optionally fixed in place, stained, etc. Only then can these sections be used in the laser microdissection system according to the invention. The operation of a microtome fundamentally differs, inter alia, from a laser microdissection system in that sections having as uniform a section thickness as possible are obtained therein. Microtomes are therefore designed to produce a large number of identical sections having parallel section areas, whereas laser microdissection systems are designed for separating dissectates according to sample-specific criteria, for example visual criteria. A person skilled in the art would therefore not transfer technical solutions used in microtomes to laser microdissection systems.

Moreover, microtomes do not comprise a microscope into the viewing beam path of which a laser beam is coupled. Therefore, the laser beam in microtomes is also never focused onto a processed sample, e.g. a block of tissue, through a microscope objective that is also used for viewing purposes.

Furthermore, a laser microdissection system having a laser scanning device is advantageously used in the context of the present invention. In laser microdissection systems having a laser scanning device, the microscope stage is arranged so as to be fixed relative to the x-y direction (i.e. in the directions perpendicular to the optical axis of the microscope objective) when the dissectate is being separated, i.e. during the dissection operation.

Unlike laser microdissection systems that have a microscope stage (scanning stage) which is moved by a motor during the dissection operation and has to have a high degree of positional accuracy particularly in the case of high-magnification objectives in order to make precise sections possible, laser microdissection systems having a laser scanning device have proven to be simpler and more cost-effective to produce and have advantages in terms of precision.

In a particularly advantageous embodiment, the laser scanning device comprises two thick, glass optical wedges which are at an angle to an optical axis, can rotate about the optical axis independently of one another, and bring about a beam deflection as a result of their wedge angles. Owing to the rotation of the glass optical wedges, the resultant deflection angle of the laser beam in relation to the optical axis is variable. As a result of the thickness and the oblique position of the glass optical wedges, at the output of the laser scanning device the laser beam has a lateral beam offset in relation to the optical axis and impinges on the centre of the objective pupil of the microscope objective at any deflection angle. The intersection point of the laser beam with the object plane is thus adjustable.

Therefore, a laser scanning device of this type is in particular advantageous over other laser scanning devices such as scanning mirrors, galvanometer scanners or step motor scanners because it does not have to be arranged in a plane that is conjugated with the objective pupil. Therefore, there is also no need for a pupil imaging in order to ensure that the deflected beam impinges on the objective pupil. In the case of microdissection using UV laser light, a pupil imaging suitable for UV would be necessary, for example. Additional advantages of a laser scanning device of this type comprising optical wedges are, for example, mentioned in EP 1 276 586 B1.

An electrophoresis unit which is "attached or can be attached by means of coupling means" should be understood to mean that the electrophoresis unit either is permanently fastened in a corresponding laser microdissection system or comprises coupling means for temporarily fastening said unit in a corresponding laser microdissection system. "Permanent" fastening can be carried out using a screw connection for example, although the possibility is not excluded of a fastening of this type being able to be released for example for the purpose of maintenance or if a corresponding laser microdissection system is being redesigned.

Coupling means provided for temporary fastening comprise attachment structures formed for example on the microscope of the laser microdissection system. The electrophoresis unit also comprises corresponding (complementary) attachment structures. For example, a laser microdissection system can have appropriate rails or recesses designed for sliding in or inserting, respectively, an electrophoresis unit. In this case, the electrophoresis unit for example has complementary rails and/or a shape which make insertion in a corresponding recess possible. Such rails, shapes and/or recesses can be designed (both on the electrophoresis unit and for example on the microscope of the laser microdissection system) such that they allow an electrophoresis unit to be attached in just one predetermined position, for example to prevent user error or to achieve a reproducible position relative to the defined reference position in the object plane.

The "defined reference position" can be any fixed point in relation to which an object is or can be secured, and which makes it possible to make reference to regions in the object. In this case, a defined reference position does not even have to be fixed in the object plane—it is sufficient for this reference position itself to have a defined location in relation to an additional reference point in the laser microdissection system used. For example, a defined reference position can be a point at which the objective axis intersects the object plane. By positioning the electrophoresis gel in parallel with the object plane and relative to the defined reference position, a gel pocket can be provided in each case as a collection device for a dissectate so that dissectates, obtained by means of the laser beam of the laser unit, from a sample that can be arranged in the object plane can be collected in the at least one gel pocket.

An "electrophoresis gel" is produced in the usual manner and can consist for example of 1% or 2% agarose having a defined melting point, optionally containing suitable additives. Said gel comprises at least one gel pocket, but preferably a plurality thereof. Details on the electrophoresis gel and the gel pockets thereof are set out below.

The laser microdissection system thus has means for positioning the electrophoresis gel having the gel pocket(s) relative to the nucleic-acid-containing sample. As a result, the dissectates can be collected in the gel pocket(s). In the process, "positioning" typically involves arranging a gel pocket below the sample or the region thereof to be dissected.

Unlike in the prior art, single cells or tissue regions (cell groups) of a nucleic-acid-containing sample can be transferred into corresponding gel pockets and examined in a targeted manner by means of the laser microdissection system according to an embodiment of the invention. Following a corresponding electrophoresis method, for example the aforementioned comet assay, the individual cells or tissue regions can be uniquely assigned to particular regions of the sample. In each case, it is thus possible to precisely assign a signal from a corresponding electrophoresis method to a defined sample region. Unlike the prior art, in which it is not possible to specifically isolate individual cells or sample regions such as tissues or cell groups, the present invention for example makes it possible to make specific, localised assessments regarding DNA damage in single cells or tissue regions of this type.

For example, the sample may be sections of fixed tissues, smears or swabs, for example of medical samples, adherent cell cultures and the like. A particular advantage of the invention is that different regions of samples of this type can be treated in different ways (e.g. by means of ionising radiation and/or mutagenic reagents) and a corresponding reaction (in the form of DNA damage) can be detected locally. Since the samples are otherwise treated in the same manner, differences resulting from the sample processing are largely avoided.

The invention also makes it possible to detect cell-specific or tissue-specific reactions to corresponding harmful factors by for example corresponding regions of a microscopic section being examined and compared with unaffected cell or tissue samples (i.e. for example those which have not been treated by means of ionising radiation and/or mutagenic reagents). This proves to be much simpler than both pre-isolation by means of alternative methods and conventionally carrying out single-cell gel electrophoresis. As mentioned, until now a cell suspension has had to be produced for this purpose, out of which the corresponding cells or tissue regions settle into the gel pockets.

In the context of an embodiment of the present invention, an "electrophoresis unit" can be designed differently depending on the level of integration of the electrophoresis in the laser microdissection system, and can in particular be equipped differently with additional components. As explained above, the electrophoresis unit for carrying out the actual electrophoresis can remain in the laser microdissection system or be removed therefrom. In the latter case, the electrophoresis unit can have a particularly simple design and can for example comprise merely the electrophoresis gel on a suitable gel carrier. In this case, means are advantageously provided which allow the electrophoresis gel to be positioned or oriented, and thus assigned, in a defined manner in the laser microdissection system, and allow the position to be stored. For example, a gel carrier can thus comprise appropriate markings relating to the orientation thereof in the laser microdissection system, the position of each individual gel pocket being defined for example with reference to a coordinate system (the defined reference position) fixed by the gel carrier or the laser microdissection system.

The electrophoresis unit can have fluid lines which either are rigidly attached thereto or can be rigidly attached thereto by means of coupling means, and which are connected to corresponding means for introducing fluid into the electrophoresis unit and/or for removing fluid therefrom. Reference is made to the above explanations for the meaning of the wording "attached or can be attached by means of coupling means". For example, corresponding fluid lines can be used to cover the electrophoresis unit with a suitable gel material, for example agarose, before the electrophoresis is carried out, and/or to introduce an electrophoresis buffer and/or suitable detection reagents. Known mixtures or compounds can be used as the electrophoresis buffers and/or detection reagents. Fluid can of course also be removed from the electrophoresis unit by means of corresponding fluid lines. Gaseous fluids can also be used, for example to dry a (closed) electrophoresis unit and/or to displace other fluids.

Advantageously, a corresponding electrophoresis unit can in fact also have suitable electrodes for applying a voltage to the electrophoresis gel. Electrodes of this type advantageously extend along two opposite sides of the electrophoresis gel.

As mentioned, a laser microdissection system according to an embodiment of the invention can be designed to carry out electrophoresis using the electrophoresis unit attached in the laser microdissection system. For this purpose, a corresponding laser microdissection system can have a fluid system and/or an electrophoresis device. The fluid system can for example comprise suitable pumps, the outputs and/or inputs of which can be connected to the above-mentioned fluid lines. The fluid system can for example be actuated by a control unit of the laser microdissection system. The same applies to an electrophoresis device, i.e. a voltage source, of which the outputs and/or inputs can be coupled to the connections of the electrodes of the electrophoresis unit. In this particularly advantageous embodiment, the invention provides a laser microdissection system comprising a fully integrated electrophoresis system.

In some cases, however, laser microdissection systems in which the electrophoresis unit for carrying out an electrophoresis method can be removed from the laser microdissection system may also be advantageous. For this purpose, said unit is formed comprising appropriate coupling means, as explained above. This for example makes a more modular design possible and allows dissectates or electrophoresis units of different laser microdissection systems to be analysed centrally at a central point and under identical conditions, in order to increase reproducibility for example. In this case, a corresponding gel carrier may also for example be suitably preserved and sent to a central laboratory.

A laser microdissection system having analysis means for analysing a result of the electrophoresis method is particularly advantageous. As explained, the laser microdissection system according to an embodiment of the invention makes it possible to uniquely assign gel pockets of the electrophoresis gel to regions of the sample. In this respect, a corresponding laser microdissection system can also be designed, for example, to move towards the assigned position in the in the respectively associated region of the sample when a specific gel pocket is specified, so that the user can immediately detect which sample region has led to a corresponding signal in the electrophoresis method. Conversely, when a particular sample region is specified, for example by a positionable sample holder moving theretowards, it is possible to display the respectively associated gel pockets (or the associated signals of the electrophoresis method). In this case, the user can also be given the option to select a region of the sample (e.g. by circling by means of a digital selection unit). On this basis, the laser microdissection system shows all the signals received in this region from the electrophoresis method. As a result, the user for example receives information relating to scattering of the received signals in a morphologically uniform region of the sample. Therefore, appropriate analysis means comprise for example control means, visual display means, motors for moving the sample holder, and selection means.

As mentioned, in general substantial advantages of the laser microdissection system according to an embodiment of the invention result from the fact that one of the one or more gel pockets can be assigned in each case to a region of the nucleic-acid-containing sample. This has already been outlined above.

An electrophoresis gel for use in an embodiment of the invention can have for example 12, 24 or 96 gel pockets. These are for example arranged in the form of a regular pattern according to known microtiter plates (in other words in "rows" and "columns" arranged at right angles to one another). The number of gel pockets is determined by the size and spatial separation thereof. The number of gel pockets is thus also determined by the sample and the size and/or number of the dissectates obtained therefrom. If a large amount of dissectate material is required or large dissectates are intended to be obtained, it is advantageous to use fewer, accordingly larger gel pockets. This also applies when a relatively long separation distance is desired. In this case, there has to be sufficient gel material between the gel pockets in order to provide this separation distance. To add reagents, for example a microtiter plate that is open at the bottom and placed on a corresponding electrophoresis gel (as described in the article by Wood et al.) can also be used. In this case the number and arrangement of the gel pockets are determined by the design of a microtiter plate of this type.

An electrophoresis gel can be pre-made or produced in a corresponding electrophoresis unit by a known casting method. Corresponding electrophoresis units can also be provided with pre-made gel inserts, which reduces the complexity of carrying out such methods. The gel pockets can for example be made therein using suitable dies when casting the electrophoresis gel therein. After the gel has "cured", the die can be removed and the gel has a corresponding number of gel pockets. To make the gel pockets, for example a die that has been produced by means of routine microstructure techniques can be used.

The diameter or the volume of the gel pockets of the electrophoresis gel is also determined by the desired signal quality that is intended to be received, for example by means of single-cell gel electrophoresis method. Typical diameters vary within a range of from 10 µm to 50 µm. Larger volumes produce stronger but possibly more diffuse signals. With lower volumes, sharper but potentially accordingly weaker signals are received. As mentioned, a key factor that influences the size or volume of the gel pockets is the amount of sample to be held.

An embodiment of the invention also relates to a corresponding electrophoresis unit for an above-mentioned laser microdissection system. An electrophoresis unit of this type is particularly advantageous if it comprises means for being reversibly attached in the laser microdissection system. These means can for example comprise the aforementioned attachment structures. As mentioned, said unit can thus be removed, for example, in order to carry out the electrophoresis and/or to introduce an electrophoresis gel. A correspondingly modular design allows an electrophoresis unit to be prepared or to be processed afterwards while another electrophoresis unit is undergoing dissection or analysis.

In an examination method according to an embodiment of the invention for nucleic-acid-containing samples, a laser microdissection system is used as explained above. The method comprises separating dissectates from a nucleic-acid-containing sample by means of a laser beam, collecting these dissectates in one or more gel pockets of the electrophoresis gel, and then examining them by means of an electrophoresis method. The examination itself (i.e. the electrophoresis method) can be carried out in a known manner (e.g. by means of the aforementioned comet assay) and may comprise introducing additional gel material for covering the gel pockets and/or introducing reagents, buffers, enzymes, fluorescence markers and the like.

As mentioned several times, an examination method according to an embodiment of the invention is particularly advantageous when each gel pocket, used for collecting, of the one or more gel pockets is assigned to a region of the sample. This makes localised examinations possible.

As also mentioned, the dissectates can be examined by means of the electrophoresis method in an "integrated" laser microdissection system while the electrophoresis unit containing the electrophoresis gel is attached in the laser microdissection system. An advantage of this may be that all the parameters of the electrophoresis method can be adjusted centrally. In this way, it may be possible to predefine a complete operating programme in which the user has to specify merely the regions to be dissected. In this case, the laser microdissection system of course carries out the additional steps and is therefore particularly user-friendly.

Reference is made to the above explanations for the advantages of the alternative option of examining the dissectates by means of the electrophoresis method after the electrophoresis unit containing the electrophoresis gel has been removed from the laser microdissection system.

The examination method is particularly advantageous if a result of the electrophoresis method is also analysed by means of the laser microdissection system. This can also involve the assignment that has been mentioned multiple times.

Figure 1:
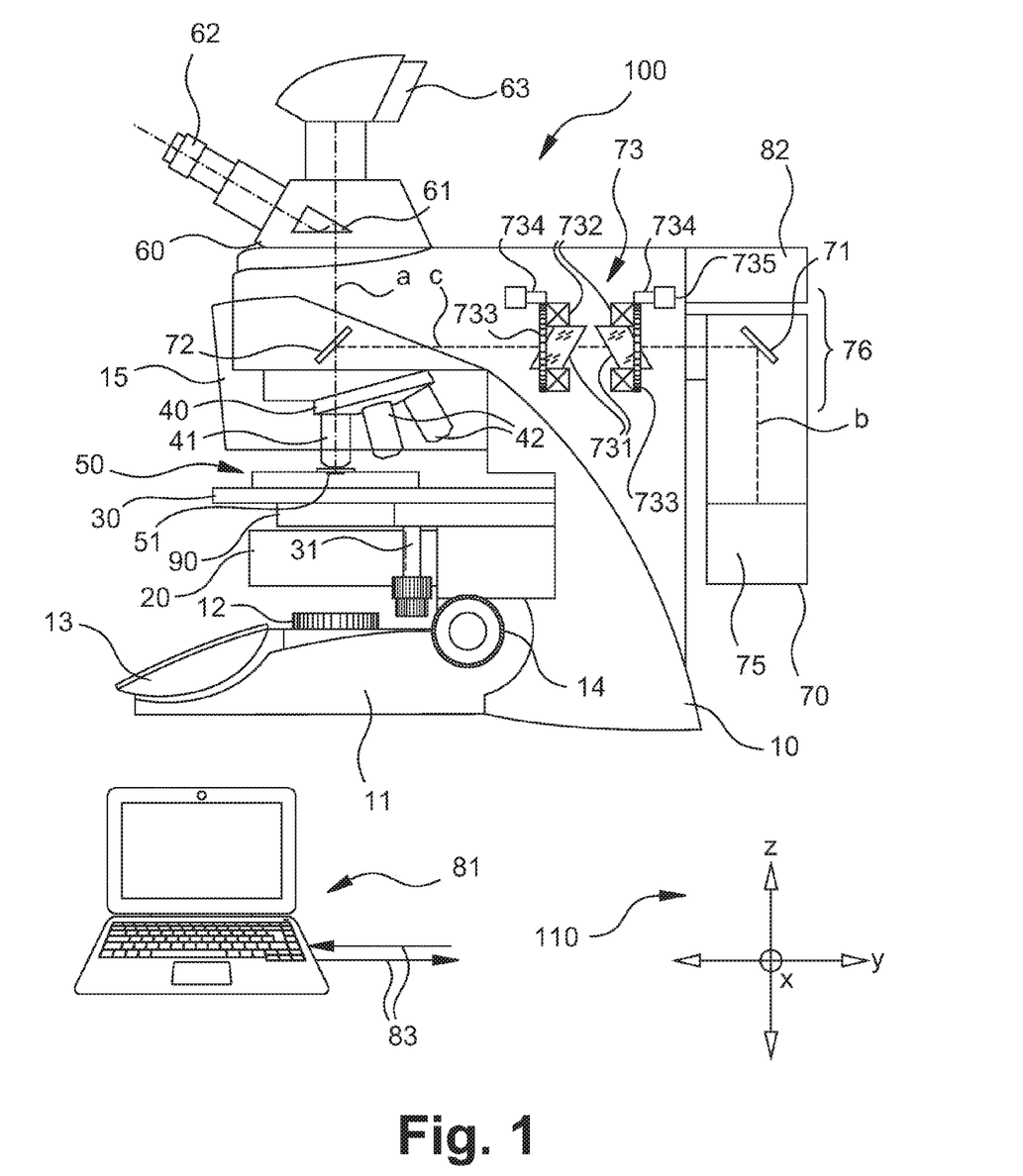
FIG. 1 shows a laser microdissection system which can be used to carry out a method according to an embodiment of the invention.

FIG. 1 is a schematic view of a laser microdissection system which can be used to carry out a method according to an embodiment of the invention and is denoted in general by 100. The essential parts of the laser microdissection system 100 correspond to those disclosed in EP 1 276 586 B1, to which reference is explicitly made here. A coordinate system, on the basis of which the axes or directions x, y and z mentioned in the following are illustrated, is denoted by 110.

The laser microdissection system 100 comprises a microscope 10. An illumination device 12, which is shown here only in part, can be provided in a microscope base 11 of the microscope 10. This can comprise for example a light source (not shown) and suitable means for influencing the illumination light provided by the light source, for example filters and/or diaphragms.

A user input unit and/or a user information unit 13, which can for example be designed as a touchscreen and by means of which the user can for example input and/or read observation and/or processing parameters, can for example also be arranged on the microscope base 11.

A pinion knob 14 is also provided. This is used to operate a coarse focus and a fine focus to adjust the height of a microscope stage 30. As a result, a sample 51 located on an object support on a sample holder 50, for example a section mounted on the object support, can be brought into a focal plane of an objective 41. The objective 41 is fastened in a revolving nosepiece 40 along with other objectives 42. For protection against laser radiation, a protective cover 15 can be provided. A condenser unit 20 is used to transilluminate the sample 51 and to adjust suitable contrast or viewing processes.

Below the sample holder 50 there is an electrophoresis unit 90, which can be equipped with an electrophoresis gel having suitable gel pockets. Details thereof are shown in the subsequent figures, FIGS. 2 and 3.

Observation light from the sample 51 extends along an observation beam path a. In a tube unit 60 having suitable decoupling devices 61, a preferably variable proportion of the observation light, preferably around 60°, can be decoupled and presented to a user by means of a pair of eyepieces 62. A further proportion of the observation light can be coupled into a digital image capture unit 63 and captured to produce an image.

The laser microdissection system 100 comprises a laser unit 70 having a laser light source 75. A laser beam b provided by the laser light source 75, which can for example be a UV laser light source, is deflected at a first deflection mirror 71 and a second deflection mirror 72 in an incident-light unit (here indicated in general by 76) and focused onto the sample 51 by the objective 41.

In the laser microdissection system 100, the location at which the laser beam b impinges on the sample 51 can in principle be adjusted in different ways. First, a manual adjustment device 31 can be provided, by means of which the microscope stage 30 formed as a mechanical stage can be moved in the x and y direction (in other words, in this case perpendicularly to and in parallel with the drawing plane, respectively). In addition to the adjustment device 31, it is also possible to provide electromechanical control means which can be actuated by a control unit 82 or the position of which can be detected by the control unit 82.

The control unit 82 can also control any other motorised functions of the laser microdissection system 100 and can in particular provide an interface to an external control computer 81, which can be connected by means of appropriate connections 83. In particular, the control computer 81 and/or the control unit 82 can be designed as means for actuating the object stage 30, the sample holder 50 and/or the electrophoresis unit 90 (see FIGS. 2 and 3).

However, a laser scanning device 73 can in particular be provided for the laser microdissection. By means of the laser scanning device 73, the laser beam b can also be deflected relative to an optical axis c extending between the first deflecting mirror 71 and the second deflecting mirror 72. Therefore, the laser beam can impinge on the second deflecting mirror 72, which can be designed for example as a dichromatic splitter, at different positions and is thus also focused onto the sample 51 at different positions. A corresponding deflection by means of a laser scanning device 73 is disclosed in detail in EP 1 276 586 B1. It should be emphasised that different options for deflecting a laser beam b or for positioning the sample 51 with respect to the laser beam b can be used. The invention is not restricted to the example shown.

In the example shown, the laser scanning device 73 comprises two solid glass optical wedges 731, which are at an angle to the optical axis c and can rotate about the optical axis c independently of one another. For this purpose, the optical wedges 731 are mounted by ball bearings 732. Each of the optical wedges is connected to a toothed wheel 733. The toothed wheels 733 can be rotated in each case by means of rotation devices 734. The rotation devices 734 can be set into rotation manually and/or by means of suitable electromechanical apparatuses, for example by means of step motors and can drive the toothed wheels 733 thereby. The rotation devices 734 can have position indicators 735 (here shown only on the right-hand rotation device 734). A position detected thereby can be transmitted to the control unit 80.

Figure 2:
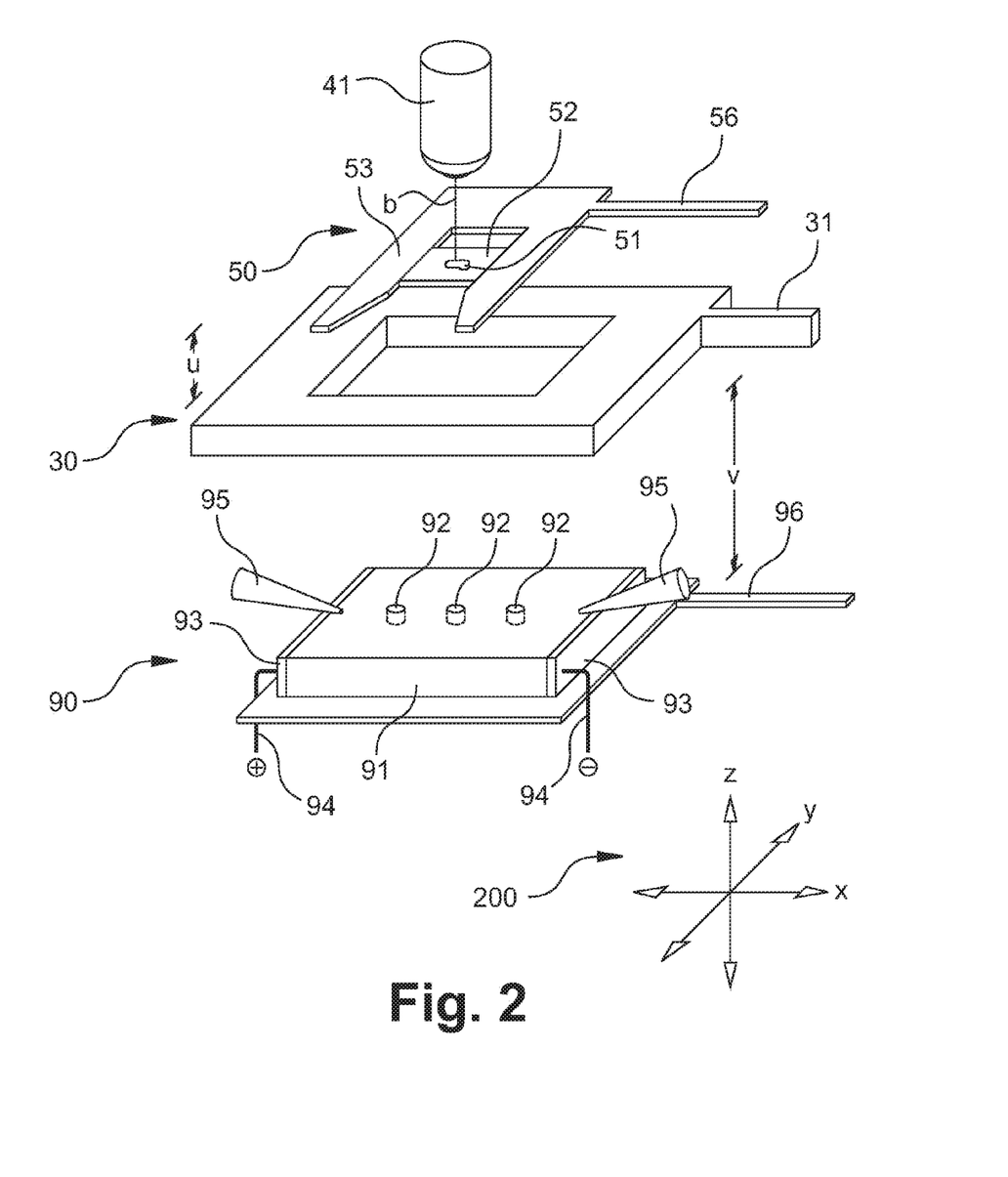
FIG. 2 is a schematic view of details of a laser microdissection system according to FIG. 1 in a first embodiment.

FIG. 2 is a schematic view of details of a laser microdissection system 100 according to FIG. 1 in a first embodiment. In this respect, parts of the sample holder 50, microscope stage 30 and electrophoresis unit 90 are shown. The microscope objective 41 is also shown. The aforementioned elements are shown in a perspective and greatly simplified view. The coordinate system used is denoted by 200. The directional indications x, y and z correspond to those in FIG. 1. The axes or directions x and z are in the drawing plane.

The sample holder 50 comprises a holding device 53, by means of which for example an object support 52 containing the sample 51 can be held. The holding device 53 can be displaced in at least one of the directions x and y by means of a displacement device 56. As a result, it is possible to displace regions of the sample 51 with respect to the laser beam b. The displacement device 56 is shown very schematically. A laser microdissection system 100 according to an embodiment of the invention can for example comprise coaxial knurled screws or rotary knobs, by means of which the holding device 53 and thus the sample 51 can be displaced in the x and y direction, as shown in FIG. 1 for the adjustment device 31 of the object stage 30.

As illustrated in the following with reference to FIG. 3, the sample 51 is typically located on the underside of an object support 52. Although the object support 52 is square in the example shown, a laser microdissection system according to an embodiment of the invention can also be equipped with a holding device 53 designed for holding conventional object supports in a width-to-height ratio of 1:3 or 1:4.

The sample holder 50 is arranged above (in the z-direction, i.e. from the viewer or objective side) the microscope stage 30. The microscope stage 30 can also be moved in at least one of the directions x and y, in particular by means of the adjustment device 31 shown very schematically here. Coaxial knurled screws can for example be provided here too. Although there is a distance u between the sample holder 50 and the sample stage 30 in the example shown, the sample holder 50 can also be directly arranged on the sample stage 30. In particular, the distance u can also be designed to be variable.

In the example shown, the electrophoresis unit 90 is arranged on the illumination side, i.e. in the z-direction below the object stage 30. The electrophoresis unit 90 can also be designed to be adjustable by means of suitable adjustment means 96. In this case, adjustment can also take place in at least one of the directions x and y. The electrophoresis unit 90 is shown very schematically in FIG. 2. Here too, a distance v between the electrophoresis unit 90 and the sample stage 30 can formed differently to the view in FIG. 2. In particular, the electrophoresis unit 90 can be arranged directly below the object stage 30.

The electrophoresis unit 90 comprises an electrophoresis gel 91 that has three gel pockets 92 in the example shown. The gel pockets 92 can be formed in any given number, shape and size in the electrophoresis gel. The gel pockets 92 can for example be produced using a suitable die that is pressed into a molten gel material used for producing the electrophoresis gel 91, for example in molten agarose. Once the gel material has cured, the gel pockets 92 are in the desired formation. In the electrophoresis gels 91 shown here, for example 24, 96 or 384 gel pockets are used. The individual gel pockets can measure significantly less than 100 μm. Typically, the diameters are for example from 10 μm to 50 μm.

The electrophoresis gel 91 is arranged between electrodes 93, to which a voltage (illustrated by + and −) can be applied via connections 94. The voltage can be adjusted, for example by means of a control unit 82 and/or the control computer 81. A suitable voltage source is provided yet not shown for the sake of clarity.

As is generally known, the samples are separated in an electrophoresis gel using a suitable separation buffer. Said buffer can be introduced into the electrophoresis unit 90 and removed therefrom by means of a fluid system having corresponding fluid lines 95. For example a suitable staining reagent, radioactive label and/or suitable enzymes can also be introduced into the electrophoresis unit 90 by means of the fluid lines 95. The introduction of corresponding fluids or the removal thereof via the respective fluid lines 95 can also be controlled by means of the control computer 81 and/or the control unit 82. For this purpose, suitable pumps are advantageously provided, although these are not shown either for the sake of clarity. As mentioned, the electrophoresis unit 90 can also be removed from the laser microdissection system 100.

Figure 3:
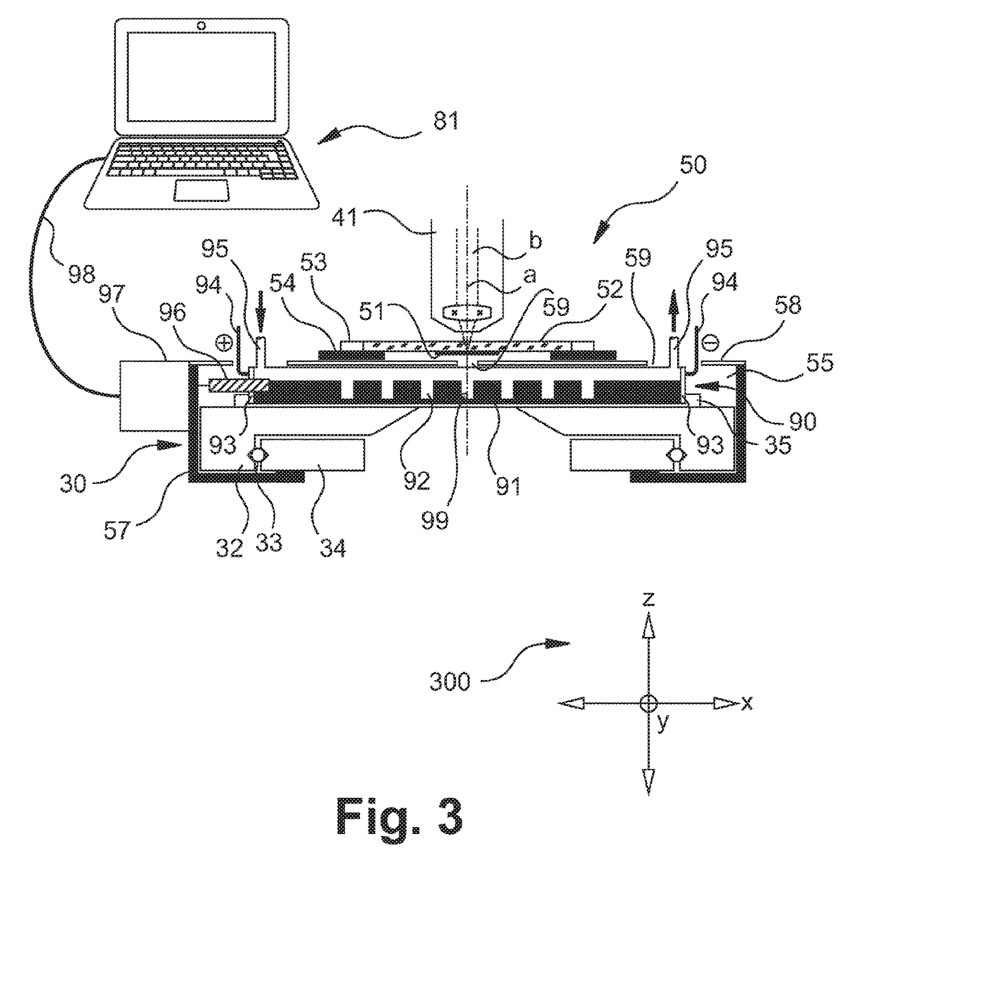
FIG. 3 is schematic view of details of a laser microdissection system according to FIG. 1 in a second embodiment.

FIG. 3 shows a cross section through the microscope stage 30, having the sample holder 50 placed thereon, in a plane spanned by the optical axis of the observation beam path a and the x-direction (perpendicular to the drawing plane of FIG. 1). The coordinate system used, together with the directions and axes, is denoted by 300.

The microscope stage 30 comprises a stationary base plate 34, on which there is arranged a plate 32 which can move in the y-direction (i.e. perpendicularly to the drawing plane). The movable plate 32 defines a stage surface of the microscope stage 30. The movable plate 32 can be displaced relative to the stationary base plate 34 by means of a suitable mechanism, for example using ball bearings 33. To reciprocally displace the stationary base plate 34 and the movable plate 32, the aforementioned adjustment device 31 can be used. Where the stationary plate 34 is described as being "fixed", this relates only to the position thereof with respect to the movable plate 32. For its part, the "stationary" base plate 34 can also be displaced in the x-direction relative to an additional plate of the microscope stage 30 and adjusted in height in the z-direction.

On the stationary base plate 34, two holding elements 57 are provided, of which only the left-hand holding element 57 is provided with a reference numeral. The holding elements 57 support an anti-contamination plate 58 that is fixed between the carrier element 54 (see below) and the electrophoresis unit 90. The anti-contamination plate 58 advantageously spans the entire stage surface of the microscope stage 30, and thus defines a free work chamber 55 at the top. The anti-contamination plate 58 is provided with cut-outs 59.

The sample holder 50 comprises a carrier element 54, on which an object support 52 can be placed. The sample 51 is attached to the underside of the object support 52. The object support 52 containing the sample 51 can be displaced in the x and/or y-direction by means of the holding device 53 mentioned above in relation to FIG. 2.

The electrophoresis unit 90 is arranged on the stage surface of the microscope stage 30. The arrangement in the example in FIG. 3 thus differs from that in FIG. 2 in that the electrophoresis unit 90 in FIG. 2 is arranged below the object stage 30, whereas in FIG. 3 it is arranged above the object stage.

The electrophoresis unit 90 is inserted into the free work chamber 55 and can for example be attached in the laser microdissection system 100 for example by coupling means 35. The electrophoresis unit 90 comprises the basic elements as explained with reference to FIG. 2, in particular an electrophoresis gel 91 (shown here hatched) in which the gel pockets 92 are made. The electrodes 93 are connected by means of corresponding lines 94, the fluid lines 95 can be used to introduce suitable fluids or conduct them away, as shown here by arrows. The electrophoresis unit 90 can also be enclosed in a suitable chamber, it being ensured that dissectates from the sample 51 can fall into the respective gel pockets 92. Suitable recesses 59 in the anti-contamination plate 58 can also be provided for the lines 94 and 95. The use of an anti-contamination plate 58 can also be omitted.

The microscope objective 51 faces the object support 52 on the optical axis of the observation beam path a (shown in dashed lines here as in FIG. 1) and generates an image of the sample 51 by means of a corresponding lens arrangement. For this purpose, the sample 51 is located in a focal plane of the microscope objective 41. Furthermore, a laser beam b coupled in as explained in relation to FIG. 1 is focused onto the sample 51 by the microscope objective 41 in order to cut out a corresponding dissectate, for example one or more single cells.

One gel pocket 92 of the electrophoresis gel 91 is arranged in each case below the sample 51 in such a way that the dissectate falls into said pocket as a result of gravity. A dissectate in a gel pocket 92 is shown very schematically and denoted by 99. As explained, the number of gel pockets 92 can be adapted to the respective requirements, for example the number of dissectates to be obtained. If an anti-contamination plate 58 is provided, one gel pocket 92 of the electrophoresis gel 91 can be arranged in each case on the optical axis of the observation beam path a below the cut-out 59. The anti-contamination plate 58 prevents dust or other particles from falling out of the surrounding air and into the respective gel pocket 92. Dissectates 99 from the sample 51 are also prevented from falling into an "incorrect" gel pocket 92 when they are ejected from the sample 51. In other words, all the other gel pockets 92 besides the desired gel pocket 92 can be closed by the anti-contamination plate 58. This permits effective analysis and prevents artefacts.

Suitable control means 97 can be connected to the adjustment device 96. The control means 97 can be designed for manual operation, yet they preferably comprise an appropriate motor which can be used to move the adjustment device 96 and the electrophoresis unit 90 attached thereto. For this purpose, the control means 97 are connected to a computer, for example the aforementioned control computer 81, by means of a corresponding connection 98. The control computer 81 or the control unit 82 displaces the electrophoresis unit 90 or the electrophoresis gel 91 by means of the control means 97 or the adjustment device 96 in such a way that the respectively desired gel pocket 92 is located on the optical axis of the observation beam path a below the cut-out 59 and thus below the region of the sample 51 that is processed by means of the laser beam b. Following each completed laser microdissection operation, the corresponding dissectate 99 falls into the respective gel pocket 92 as a result of gravity. Where necessary, the control computer 81 will then position another gel pocket 92 or an empty gel pocket accordingly in order to thus collect one or more new dissectates.

Once a desired number of dissectates have been obtained and collected in the gel pockets 92, electrophoresis can be initiated, for example by introducing a suitable buffer into the electrophoresis unit 91 by means of the fluid lines 95. The electrophoresis gel 91 may also have been covered beforehand with gel material supplied via the fluid lines 95. By applying a voltage to the electrodes 93 via the lines 94, a voltage gradient is generated which causes electrophoresis of the dissectates held in each case. In this connection, the comet assay described at the outset can in particular be carried out.

Following the electrophoresis method, the success thereof can be checked directly by means of the objective 41.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

The invention claimed is:

1. A laser microdissection system comprising:
    a microscope comprising:
        an incident-light device,
        a microscope objective, and
        a laser unit operable to produce a laser beam having a beam path extending through the incident-light device and through the microscope objective and intersecting an object plane of the microscope objective at an adjustable intersection point;
    wherein dissectates of a sample that can be disposed in the object plane are obtained using the laser beam, an electrophoresis unit disposed below the object plane and containing an electrophoresis gel including one or more gel pockets, the electrophoresis unit being operable to be attached by a coupling device;

a positioning device operable to position the electrophoresis gel in parallel with the object plane and relative to a defined reference position such that the obtained dissectates of the sample can be collected in the one or more gel pockets; and an assignment device operable to assign one or more of the one or more gel pockets respectively to one or more regions of the sample such that one or more of the obtained dissectates collected in the one or more gel pockets are correlated to one or more defined regions of the sample.

2. The laser microdissection system according to claim 1, wherein the electrophoresis unit comprises fluid lines for one or more of introducing fluid into the electrophoresis unit and removing fluid from the electrophoresis unit.

3. The laser microdissection system according to claim 1, wherein the electrophoresis unit comprises electrodes for applying a voltage to the electrophoresis gel.

4. The laser microdissection system according to claim 1, further comprising: a fluid system for carrying out an electrophoresis method by the electrophoresis unit attached in the laser microdissection system.

5. The laser microdissection system according to claim 4, further comprising an analyzer operable to analyze a result of the electrophoresis method once the electrophoresis method has been completed.

6. The laser microdissection system according to claim 1, wherein the electrophoresis unit, for carrying out an electrophoresis method, can be removed from the laser microdissection system.

7. The laser microdissection system according to claim 1, wherein the electrophoresis gel comprises 12 gel pockets, 24 gel pockets, or 96 gel pockets.

8. The laser microdissection system according to claim 1, wherein at least one of the one or more gel pockets has a diameter of 10 μm to 50 μm.

9. The laser microdissection system according to claim 1, further comprising a reversible attachment device operable to attach the electrophoresis unit in the laser microdissection system.

10. An examination method for nucleic-acid-containing samples, in which a laser microdissection system is used, the laser microdissection system having a microscope including an incident-light device, a microscope objective, and a laser unit, the method comprising:

disposing the nucleic-acid-containing sample in an object plane of the microscope objective, separating dissectates from the nucleic-acid-containing sample via a laser beam produced by the laser unit, the laser beam having a beam path extending through the incident-light device and through the microscope objective and intersecting the object plane at an adjustable intersection point, collecting the dissectates in one or more gel pockets of an electrophoresis gel of an electrophoresis unit disposed below the object plane by positioning the electrophoresis gel in parallel with the object plane of the microscope objective and relative to a defined reference position such that the dissectates can be collected in the one or more gel pockets, and assigning one or more of the one or more gel pockets respectively to one or more regions of the sample, such that one or more of the separated dissectates collected in the one or more gel pockets are correlated to one or more defined regions of the sample, and examining the dissectates using an electrophoresis method.

11. The examination method according to claim 10, wherein each of the one or more gel pockets is assigned to a region of the nucleic-acid-containing sample.

12. The examination method according to claim 10, wherein the dissectates are examined by the electrophoresis method while the electrophoresis unit containing the electrophoresis gel is attached to the laser microdissection system.

13. The examination method according to claim 10, wherein the dissectates are examined using the electrophoresis method after the electrophoresis unit containing the electrophoresis gel has been removed from the laser microdissection system.

14. The examination method according to claim 10, wherein a result of the electrophoresis method is also analysed by the laser microdissection system.

* * * * *